US012685742B2

(12) United States Patent
Wang et al.

(10) Patent No.: US 12,685,742 B2
(45) Date of Patent: Jul. 21, 2026

(54) APPLICATION OF STACHYOSE IN PREPARATION OF DRUG FOR TREATING CASTRATION-RESISTANT PROSTATE CANCER

(71) Applicant: Jiangnan University, Wuxi (CN)

(72) Inventors: Rong Wang, Wuxi (CN); Yongquan Chen, Wuxi (CN); Lu Xu, Wuxi (CN); Xiaoying Wang, Wuxi (CN); Shenglong Zhu, Wuxi (CN)

(73) Assignee: Jiangnan University, Wuxi (CN)

( * ) Notice: Subject to any disclaimer, the term of this patent is extended or adjusted under 35 U.S.C. 154(b) by 914 days.

(21) Appl. No.: 17/860,451

(22) Filed: Jul. 8, 2022

(65) Prior Publication Data

US 2022/0339175 A1      Oct. 27, 2022

Related U.S. Application Data

(63) Continuation of application No. PCT/CN2021/108363, filed on Jul. 26, 2021.

(30) Foreign Application Priority Data

Jul. 1, 2021    (CN) .......................... 202110744184.2

(51) Int. Cl.
    *A61K 31/702*     (2006.01)
    *A61K 31/4166*    (2006.01)
    *A61P 13/08*      (2006.01)
    *A61P 35/00*      (2006.01)

(52) U.S. Cl.
    CPC ........ *A61K 31/702* (2013.01); *A61K 31/4166* (2013.01); *A61P 13/08* (2018.01); *A61P 35/00* (2018.01)

(58) Field of Classification Search
    CPC ... A61K 31/702; A61K 31/4166; A61P 13/08; A61P 35/00
    See application file for complete search history.

(56) References Cited

FOREIGN PATENT DOCUMENTS

JP        S5777620 A      5/1982
WO      2009026152 A1    2/2009

OTHER PUBLICATIONS

Dyshlovoy et al. (Scientific Reports, 2020, vol. 10, article 9764) (Year: 2020).*
Brigger et al. (Advanced Drug Delivery Reviews, 2012, vol. 64, pp. 24-36) (Year: 2012).*
Clarke et al. (Lancet Oncol, 2018, vol. 19, pp. 975-986) (Year: 2018).*
Foucquier. J.; Guedj, M. "Analysis of drug combinations: current methodological landscape", Pharmacology Research and Perspectives 2015, vol. 3, e00149. (Year: 2015).*
Shafi, A. A.; et al. "Androgen receptors in hormone-dependent and castration-resistant prostate cancer", Pharmacology and Therapeutics 2013, vol. 140, pp. 223-238. (Year: 2013).*
Jia, Shaohua et. al. "Study on content comparision of Stachyose in Rehmannia"s different procssed product and anti-tumor activity of Stachyose" Heilongjiang Medicine Journal V25 No. 4 2012.
Zhong, Xianfeng et. al. "Inhibiting effect of stachyose from Stachys floridana schuttl ex benth on proliferation of Caco-2 cell line and its potential mechanism" Food and Machinery V 31 No. 6, Nov. 30, 2015.
Huang, Guidong et. al. "Stachyose-induced apoptosis of Caco-2 cells via the caspase dependent mitochondrial pathway" Food Func. 2015, 6, 765-771.
Hsiao, Ya-li et. al. "Treatment of acute lymphoblastic leukemia from traditional Chinese medicine" Evidence-Based Complementary and Alternative Medicine, V 2014, ARt. ID 601064.
Huang, Bin "Effect of ethyl pyruvate on prostate cancer and mechanism study" Thesis database. Jan. 15, 2019, V01.
Wang et al., "Identification of PRDX5 as A Target for The Treatment of Castration-Resistant Prostate Cancer," Adv. Sci., 2304939:1-15, 2023.
Liu et al., "Actin cytoskeleton vulnerability to disulfide stress mediates disulfidptosis," Nat. Cell. Biol., 25:404-414, 2023.

* cited by examiner

*Primary Examiner* — Andrea Olson
*Assistant Examiner* — Benjamin M Brandsen
(74) *Attorney, Agent, or Firm* — IPro, PLLC; Na Xu

(57)                ABSTRACT

Disclosed is an application of Stachyose in preparation of a drug for treating castration-resistant prostate cancer, belonging to the technical field of biological medicine. The disclosure proposes a new strategy of using Stachyose in combination with an androgen receptor antagonist to prepare a drug for treating CRPC for the first time, and conducts multi-angle and multi-level verification research. The drug composition of the Stachyose in combination with the androgen receptor in the disclosure can be used for treating castration-resistant prostate cancer, and significantly improves the effect of Enzalutamide on inhibiting castration-resistant prostate cancer. The natural compound is applied to the advanced stage of cancer, and has important clinical therapeutic significance.

7 Claims, 8 Drawing Sheets

APPLICATION OF STACHYOSE IN PREPARATION OF DRUG FOR TREATING CASTRATION-RESISTANT PROSTATE CANCER

TECHNICAL FIELD

The disclosure belongs to the technical field of biological medicine, and particularly relates to an application of Stachyose in preparation of a drug for treating castration-resistant prostate cancer.

BACKGROUND

Androgen deprivation therapy is the standard treatment for advanced prostate cancer, but patients eventually progress to castration-resistant prostate cancer (CRPC) after an average of 1-3 years of treatment. The so-called CRPC refers to prostate cancer that has progressed after initial continuous androgen deprivation therapy (ADT). Since Docetaxel was shown to prolong overall survival in patients with metastatic castration-resistant prostate cancer (mCRPC) in 2004, in recent years, drugs such as Abiraterone acetate, Enzalutamide and Cabazitaxel have emerged for the disease stage of mCRPC, which have changed the treatment status of these patients, but ultimately it is difficult to completely reverse CRPC. Therefore, finding effective other therapeutic targets or drug combination treatment strategies is another research hotspot in the treatment of CRPC.

In recent years, cellular plasticity has emerged as an escape model for targeted diagnostics, and is a common feature of tolerance in many cancers. Blocking new drug-tolerant pathways can effectively inhibit persister cells. For example, a GPX4 lipid peroxidation pathway is an effective target that is highly expressed in many persistent cell states. So far, it is unclear whether CRPC tumors have persister cells and whether new effective targets can be found. Therefore, this study focused on the LNCaP-persister cell of prostate cancer produced by EPI-001 and Enzalutamide to find effective combination drugs for the treatment of CRPC.

EPI-001 (EPI) is an inhibitor of AR and AR-splice variants (AR-Vs) awaiting clinical development with potential for the treatment of CRPC. The target of EPI against CRPC mainly aims at an N-terminal domain (NTD). Enzalutamide (Enza) is the first approved second-generation AR antagonist with 5-8 times higher affinity for AR than traditional anti-androgens. In 2012, the US FDA approved Enza for CRPC patients accordingly. However, whether it is EPI or Enza, the treatment of CRPC generally develops drug tolerance in about 18 months. Therefore, other means are urgently needed to overcome drug tolerance and delay CRPC.

SUMMARY

The technical problem to be solved by the disclosure is to overcome the drug tolerance of the existing drugs mentioned above, and provide a drug for effectively treating CRPC, namely combination of Enza and Stac, so as to significantly improve a curative effect on CRPC and exert an excellent synergistic effect.

Stachyose (Stac) is a saccharide formed by combining 2 a-galactoses with a 1,6-glycosidic bond on a glucosyl side of sucrose, and the molecular formula is $C_{24}H_{42}O_{21}$.

A first objective of the disclosure is to provide an application of Stac in preparation of a drug for treating castration-resistant prostate cancer.

In an implementation of the disclosure, the application includes: combining Stac with an androgen receptor antagonist to prepare a drug for treating castration-resistant prostate cancer.

A second objective of the disclosure is to provide a method for treating castration-resistant prostate cancer, including: administering an effective amount of Stachyose to a castration-resistant prostate cancer patient in need.

A third objective of the disclosure is to provide a drug composition for treating castration-resistant prostate cancer. The composition includes Stac and an androgen receptor antagonist.

In an implementation of the disclosure, a mass ratio of an androgen receptor antagonist to Stac is (1-8):1, and preferably, a mass ratio of Enza to Stac is 1-3:1.

In an implementation of the disclosure, the androgen receptor antagonist includes any one or more of the following: Enzalutamide (Enza), EPI-001 (EPI), Abiraterone, and Olaparib.

In an implementation of the disclosure, the drug composition also includes pharmaceutical excipients.

In an implementation of the disclosure, the pharmaceutical excipients include a solvent, a propellant, a solubilizer, a cosolvent, an emulsifier, a colorant, an adhesive, a disintegrant, a filler, a lubricant, a wetter, an osmotic pressure regulator, a stabilizer, a glidant, a flavoring agent, a preservative, a suspending aid, a coating material, an aromatic agent, an anti-binding agent, an integration agent, a penetration enhancer, a pH regulator, a buffer, a plasticizer, a surfactant, a foamer, a defoamer, a thickener, an inclusion agent, a humectant, an absorbent, a diluent, a flocculant, a deflocculant, a filter aid, and a release retardant.

In an implementation of the disclosure, the dosage forms of the preparation include injections, lyophilized powder for injection, controlled-release injections, liposome injections, suspensions, implants, emboli, capsules, tablets, pills, and oral liquids.

In an implementation of the disclosure, the drug composition may also include drug carriers.

In an implementation of the disclosure, the drug carriers include microcapsules, microspheres, nanoparticles and liposomes.

In an implementation of the disclosure, after a lot of research and exploration, the disclosure finds a drug for treating CRPC, namely combination of Enza and Stac. The research results show that by establishing EPI and Enza-tolerant prostate cancer LNCaP-drug-tolerant persisters (L-DTP) cell strains, LNCaP cells develop recoverable drug tolerance to EPI and Enza, the combination of Enza and Stac can significantly inhibit the cell growth, the effect of drug combination is verified by CCK8 cell proliferation analysis, and the synergistic effect is determined by a CI value. At the same time, a C-MYC-over-expressed prostate cancer mouse model is constructed to compare the differences of the effects of Enza and Stac alone and in combination in the treatment of CRPC in animals, the synergistic effect generated by the drug combination greatly improves the inhibiting effect of Enza or Stac alone on CRPC, and the synergistic effect of Enza and Stac is verified in vivo and in vitro.

In an implementation of the disclosure, an L-DTP recoverable drug-tolerant cell strain is established, and a CI value is calculated by a CCK8 method and Calcusyn software. The results show that in this cell strain, compared with Enza or Stac administered alone, the in-vitro combination of Enza and Stac has a synergistic anti-CRPC effect. By establishing a C-MYC-over-expressed prostate cancer mouse model, an Enza and Stac combination group in animals is determined under a model of tolerance generation after long-term use of Enza, which has a more significant anti-CRPC model effect in vivo than a single-drug group.

The Disclosure has the Following Beneficial Effects

The disclosure proposes a new strategy of using Stac to prepare a drug for treating CRPC, and a new strategy for treating CRPC based on the combination of Enza and Stac for the first time. The disclosure will promote the application of Enza and Stac in the clinical treatment of prostate cancer, and is of great significance. It takes an average of 8-10 years for drug research from compound molecules to clinical trials, and requires a lot of human and material resources, resulting in huge time cost and economic cost. The scheme of the disclosure can realize the reuse of natural compound oligosaccharides, and can greatly shorten the time from drug discovery to clinical transformation.

DETAILED DESCRIPTION

The disclosure is further described below with reference to the accompanying drawings of the specification and specific examples, but the examples do not limit the disclosure in any form. Unless otherwise specified, the reagents, methods and devices used in the disclosure are conventional reagents, methods and devices in the technical field.

Unless otherwise specified, the reagents and materials used in the following examples are commercially available.

Example 1: Process of Using EPI and Enza to Produce DTP/DTEP in Prostate Cancer LNCaP Cells and Characteristics of this Model EPI and Enza-tolerant prostate cancer L-DTP cell strains L-DTP-EPI and L-DTP-Enza can inhibit the protein expression of AR and targets thereof, and the cell growth inhibition manifests as cycle arrest in a G0/G1 phase.

1. Experimental Method:

$1 \times 10^6$ LNCaP cells were inoculated in a 10 cm cell culture dish, and after adherence on the second day, EPI and Enza were respectively added for treatment for 9 days. In the period, for replacement, a fresh drug-containing medium was used every three days for culture, some cells (DTP cells) were collected for subsequent experiments after 9 days, and the remaining cells continued to be treated with drugs. In the period, for replacement, a fresh drug-containing medium was used every three days for culture, and DTEP cells were collected after 33 days for subsequent experiments. After the DTP and DTEP cells were produced, the cells were digested and counted to calculate the percentage of the cells in $1 \times 10^6$ cells. The collected NC, DTP and DTEP cells were used for subsequent Western Blot experiments: the three groups of cells were subjected to cell lysis, protein extraction and quantification, SDS-PAGE gel electrophoresis, membrane transfer, blocking, primary antibody incubation, secondary antibody incubation and development, then, the expression changes of AR-FL and its related target proteins and AR-Vs and its related target proteins were observed, and the expression changes of cell cycle-related proteins were observed. Flow cytometry: dead cells were stained by a PI-stained cycle kit, and cell cycle changes were determined by a flow cytometry.

Figure 1:
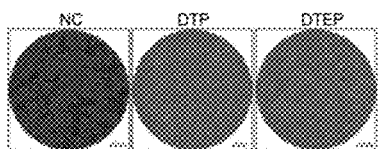
FIG. 1 shows a forming process of DTP (drug-tolerant persisters) and DTEP (drug-tolerant expanded persisters) cells in Example 1.
Figure 1:
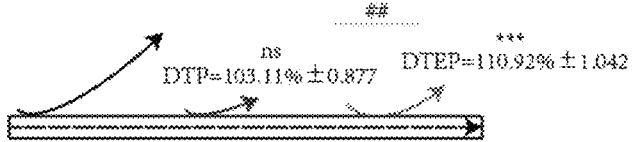
Figure 2:
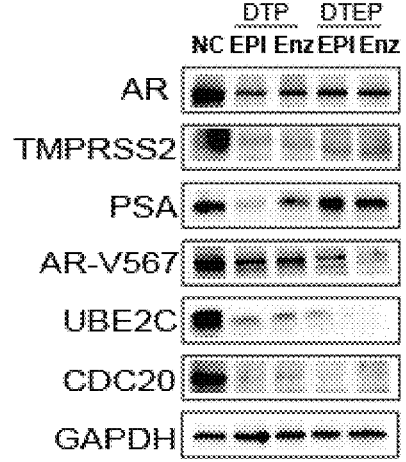
FIG. 2 shows characteristics of expression changes of AR-related proteins in the DTP and DTEP cells in Example 1.
Figure 2:
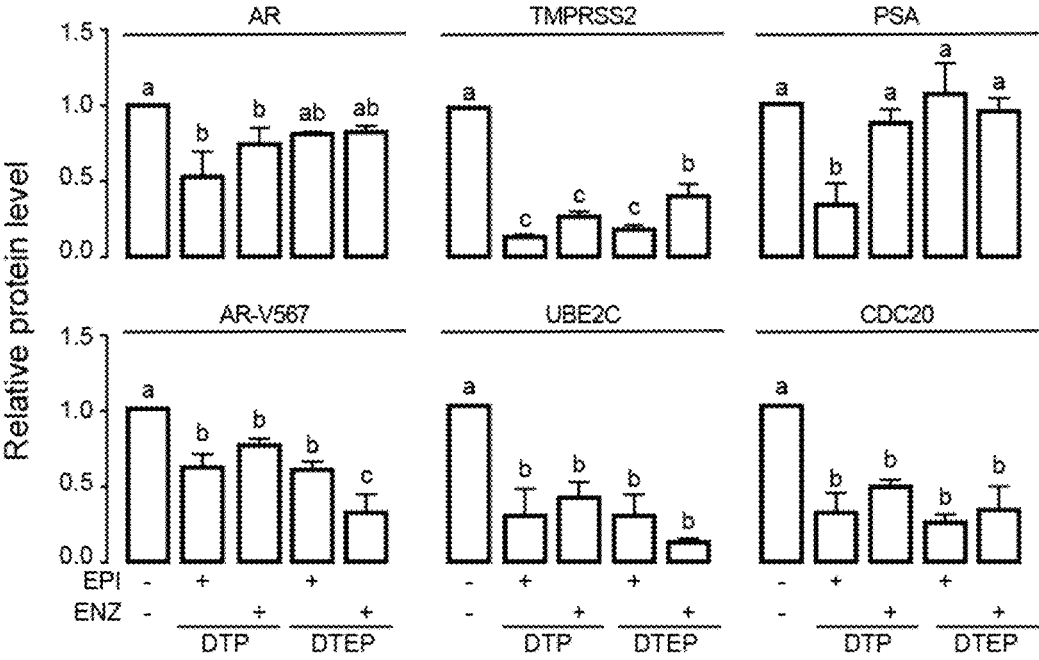
Figure 3:
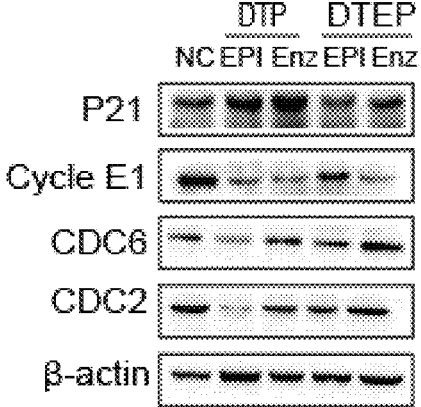
FIG. 3 shows cycle effects of the DTP and DTEP cells in Example 1.
Figure 3:
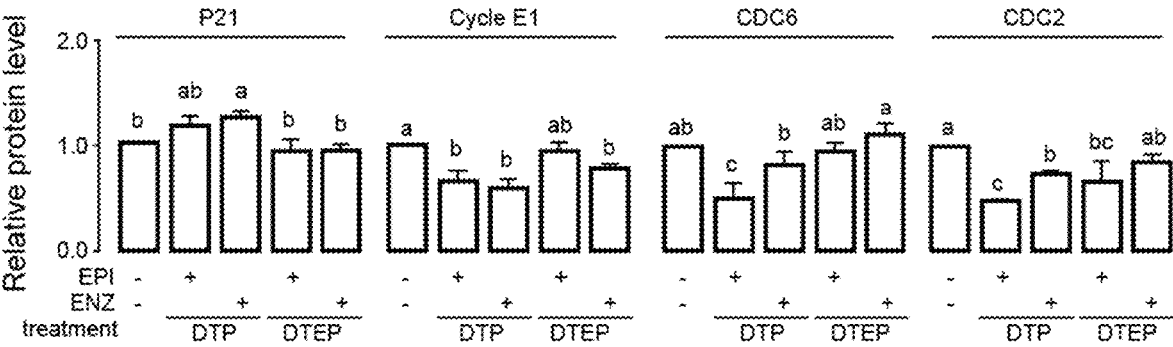
Figure 3:
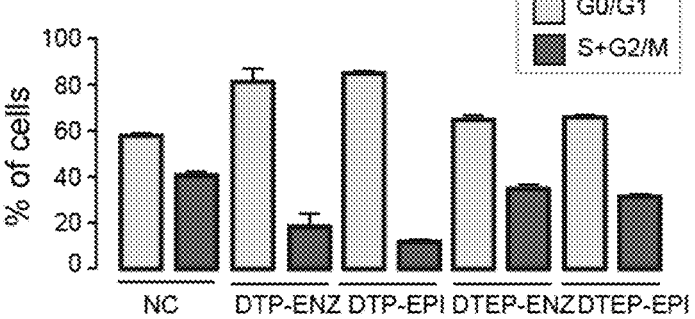

2. The results were shown in FIG. 1, FIG. 2 and FIG. 3. FIG. 1 shows a Giemsa staining graph of DTP and DTEP cells. FIG. 2 shows protein expression changes of AR & its targets and AR-Vs & its targets in NC, DTP and DTEP cells. FIG. 3 shows expression changes of cell cycle-related proteins in NC, DTP and DTEP cells.

The results showed that the number of the LNCaP-DTP cells produced by EPI and Enza accounted for 103.11% of the initial seed cells, and the LNCaP-DTEP cells accounted for 110.92%. These drug-tolerant cells were tolerant to EPI and Enza, and the cells became spindle-shaped and the growth was inhibited in DTP. In DTEP, cell clones were increased, cell growth inhibition was resisted, and cells were re-proliferated. The effects of this cell model on the protein expressions of an androgen receptor (AR) and its targets: the protein expression of AR was inhibited in a DTP state, and the expression of AR was recovered to a certain extent in DTEP; and the expression of targets TMPRSS2 and PSA of AR kept the same trend as AR. Protein expression effects of androgen receptor splice variants (AR-Vs) and their targets: in DTP and DTEP states, the protein expressions of AR-Vs and their targets UBE2C and CDC20 were continuously inhibited. This inhibition was caused by cell cycle arrest and was specifically manifested as follows: P21 (marker in G1 phase) was up-regulated in DTP, and recovered to a certain extent in DTEP; Cyclin E1 (marker in G1-S phase) and CDC6 (marker in G1-S phase) were down-regulated in DTP, and recovered to a certain extent in DTEP; and CDC2 (marker in G1-S and G2-M phases) was down-regulated in DTP, but not significantly recovered in DTEP. Through flow cytometry (FACS) analysis, it was found that the G0/G1 phase was arrested in DTP and recovered in DTEP.

Example 2: In-Vitro Effects of EPI and Enza in Combination with Stac Respectively Furthermore, CCK8 was used alone or in combination in drug-tolerant L-DTP cells to demonstrate an anti-tumor effect of Stac in drug-tolerant L-DTP (EPI) and L-DTP (Enza) cells in vitro.

1. Experimental Method:

Drug-tolerant cells L-DTP (including L-DTP (EPI) and L-DTP (Enza)) were inoculated in a 96-well plate, and after adherence, a series of Stac drugs with concentrations from high to low were prepared to find an optimal Stac drug concentration. Then, this concentration was used for measuring the survival rates of single (L-DTP (EPI)-Stac) and combined [L-DTP (EPI)-combination (EPI+Stac)] and [L-DTP (Enza)-combination (Enza+Stac)] in drug-tolerant cells L-DTP respectively. Finally, Calcusyn software was used for calculating a CI value in L-DTP cells.

Figure 4A:
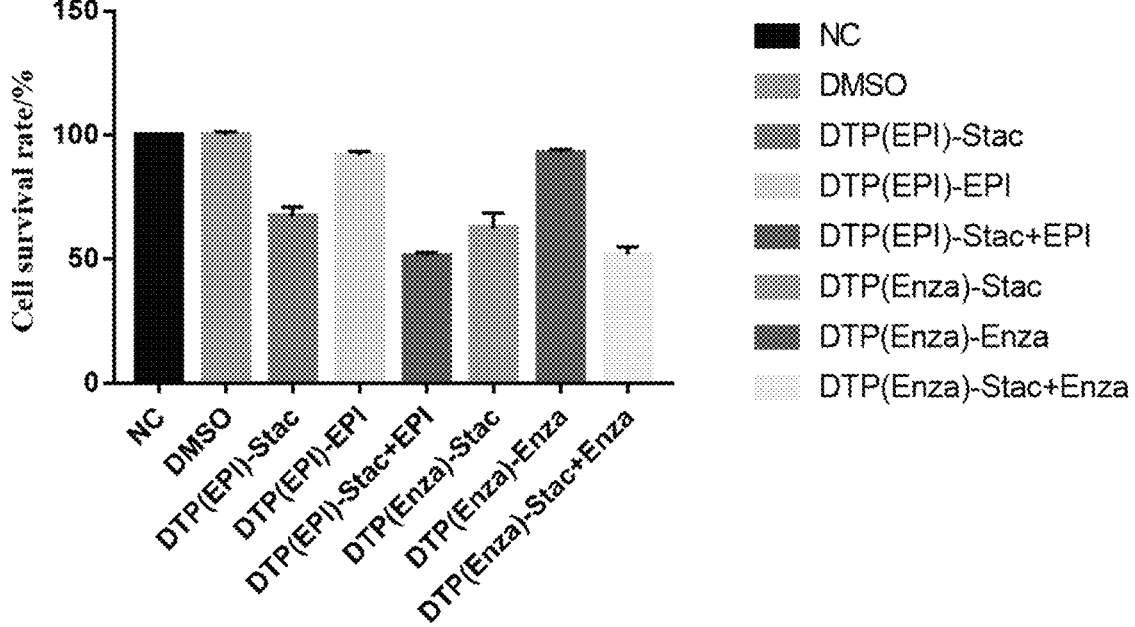
FIG. 4A shows a bar graph of a relative survival rate of drug combination cells on L-DTP-EPI and L-DTP-Enza cells in Example 2.
Figure 4B:
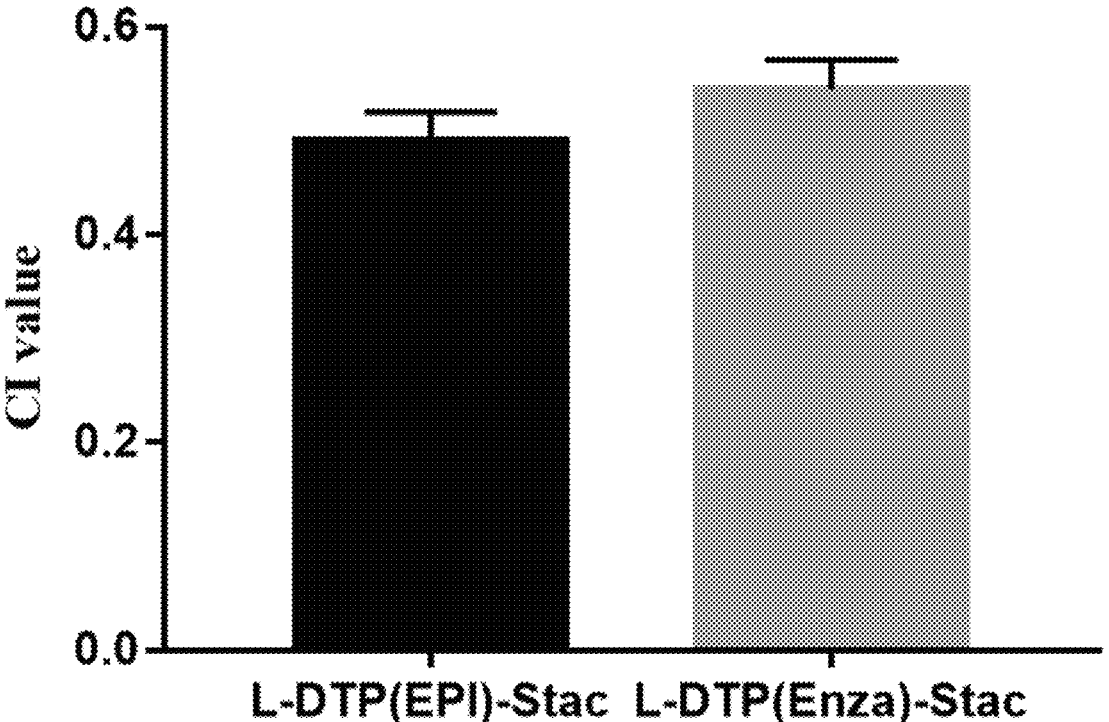
FIG. 4B shows a bar graph of a CI value of EPI and Enza in combination with Stac respectively on the L-DTP-EPI and L-DTP-Enza cells.

2. The results were shown in FIG. 4A and FIG. 4B. FIG. 4A and FIG. 4B show in-vitro pharmacodynamic graphs of EPI and Enza in combination with Stac respectively in L-DTP cells, and FIG. 4A shows a bar graph of a relative survival rate of drug combination cells on L-DTP (EPI) and L-DTP (Enza) drug-tolerant cells; and FIG. 4B shows a bar graph of a CI value of EPI and Enza in combination with Stac respectively on the L-DTP (EPI) and L-DTP (Enz) drug-tolerant cells.

The results showed that in the drug-tolerant L-DTP (EPI) cells produced after continuous administration of EPI for 9 days, and if EPI continued to be added, there was no obvious inhibiting effect; if Stac was added alone, a significant inhibiting effect was achieved, and an inhibition rate was 67.48%; and when EPI and Stac were combined, an inhibition rate was 51.15%. Similarly, in the drug-tolerant L-DTP (Enza) cells produced after continuous administration of Enza for 9 days, if Enza continued to be added, there was no obvious inhibiting effect; if Stac was added alone, a significant inhibiting effect was achieved, and an inhibition rate was 62.47%; and when Enza and Stac were combined, an inhibition rate was 51.97%. By calculating the CI value, it was found that Stac can achieve a high synergistic effect of 0.49 in L-DTP-EPI cells and a high synergistic effect of 0.54 in L-DTP (Enza) cells.

Example 3: Drug Combination Effects of Enza and Stac Combination Scheme on C-MYC-Over-Expressed Prostate Cancer Mouse Model after Generation of Tolerance by Continuous Administration of Enza Further, the effect of Enza and Stac combination in mice relapsing after chemical castration (continuous administration of Enza) was illustrated in a prostate cancer mouse model.

1. Experimental Method:

A C-MYC (Hi-Myc)-over-expressed spontaneous prostate cancer mouse model was constructed, and at 4 months, the mice developed mPIN/Cancer transition. At the moment, the mice were randomly divided into an NC control group (intragastrical administration with solvents) and an Enza administration group. Then, intragastrical administration was performed every three days, and Enza administration was performed at 10 mg/Kg for a total of 30 days. Then, the necks of some mice were severed, and the prostate cancers of the mice were taken, photographed and weighed. It was found that Enza can significantly reduce the symptoms, and the prostate weight was reduced by half compared with that in the NC control group. Then, according to the above method, the remaining mice were administered for 30 days, and it was found that some mice in the Enza group relapsed. Then, mice (mice aged 6 months) were randomly divided into: an NC control group (intragastrical administration with solvents all the time), an Enza single-drug group 1, an Enza single-drug group 2, a Stac single-drug group 1, a Stac single-drug group 2 and an Enza and Stac combination group, the corresponding administration treatment was performed, and all mice were intragastrically administered once every three days. The dosage of Enza in the Enza single-drug group 1 was kept at 10 mg/Kg each time, the dosage of Enza in the Enza single-drug group 2 was kept at 90 mg/Kg each time, the dosage of Stac in the Stac single-drug group 1 was kept at 80 mg/Kg each time, the dosage of Stac in the Stac single-drug group 2 was kept at 90 mg/Kg each time, the dosages of Enza and Stac in the Enza and Stac combination group were kept at 10 mg/Kg and 80 mg/Kg each time, and the administration was performed for a total of 30 days. Then, the necks of the mice were severed, and the prostate cancers of the mice were taken, photographed, weighed and subjected to experiments including immunohistochemistry.

Figure 5A:
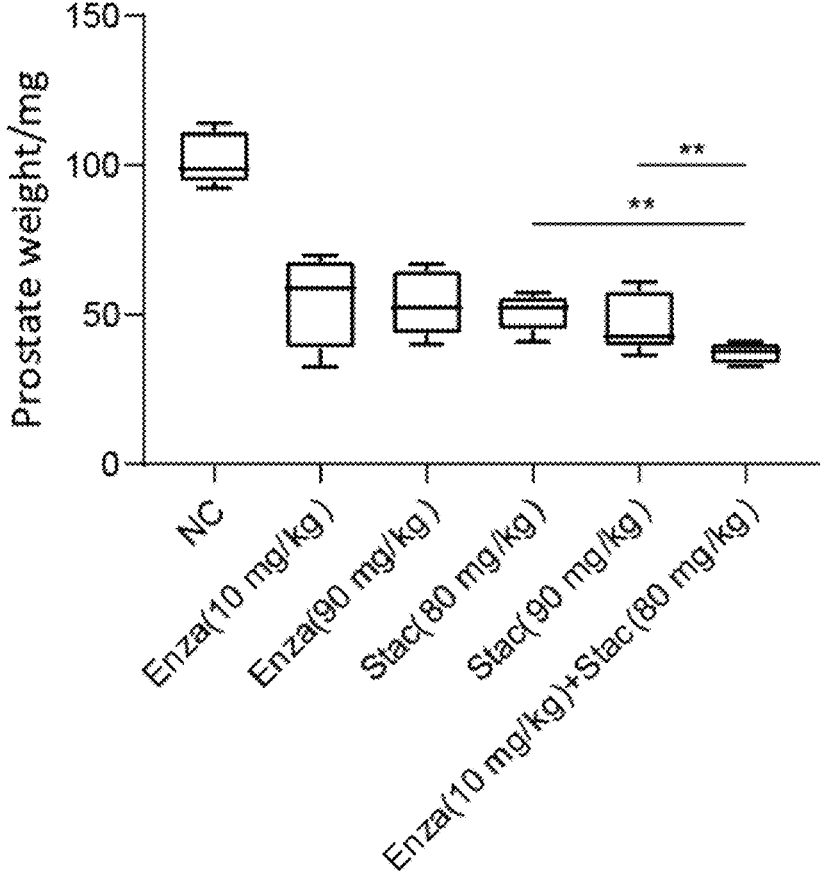
FIG. 5A shows a graph of changes in prostate weight of mice in an Enza single-drug group 1 (10 mg/Kg), an Enza single-drug group 2 (90 mg/Kg), a Stac single-drug group 1 (80 mg/Kg), a Stac single-drug group 2 (90 mg/Kg) and an Enza and Stac combination group (10 mg/Kg+80 mg/Kg) with administration in Example 3.
Figure 5B:
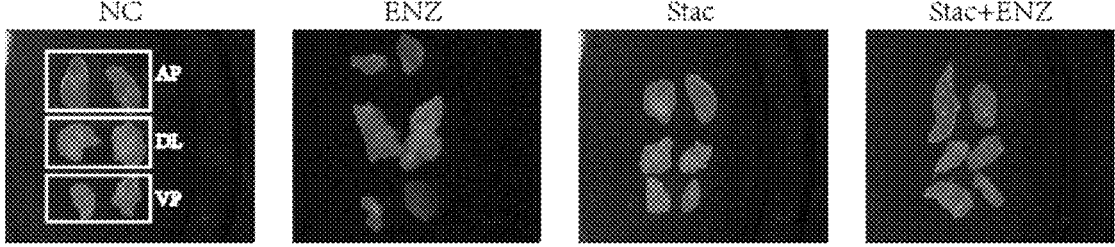
FIG. 5B shows photographs of stripped prostates of mice in the Enza single-drug group 1 (10 mg/Kg), the Stac single-drug group 1 (80 mg/Kg) and the Enza and Stac combination group (10 mg/Kg+80 mg/Kg) in Example 3.
Figure 5C:
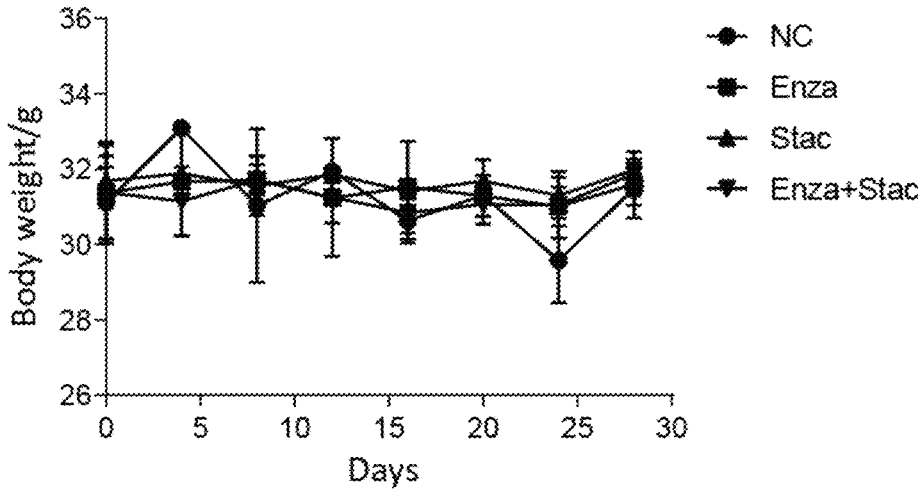
FIG. 5C shows a graph of changes in body weight of mice in the Enza single-drug group 1 (10 mg/Kg), the Stac single-drug group 1 (80 mg/Kg) and the Enza and Stac combination group (10 mg/Kg+80 mg/Kg) with administration in Example 3.
Figure 6A:
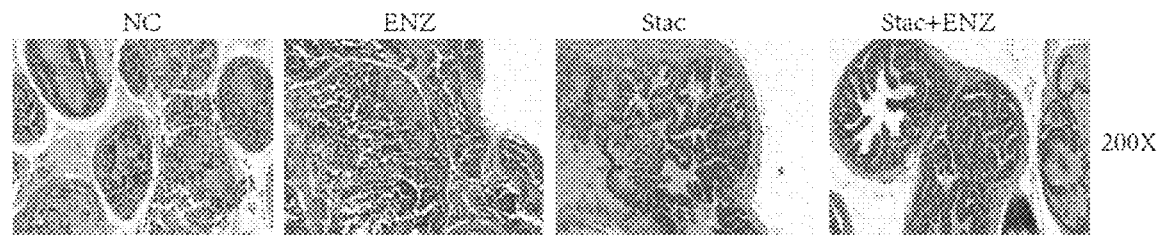
FIG. 6A shows HE staining graphs of prostate tissue slices of mice in the Enza single-drug group 1 (10 mg/Kg), the Stac single-drug group 1 (80 mg/Kg) and the Enza and Stac combination group (10 mg/Kg+80 mg/Kg) in Example 3.
Figure 6B:
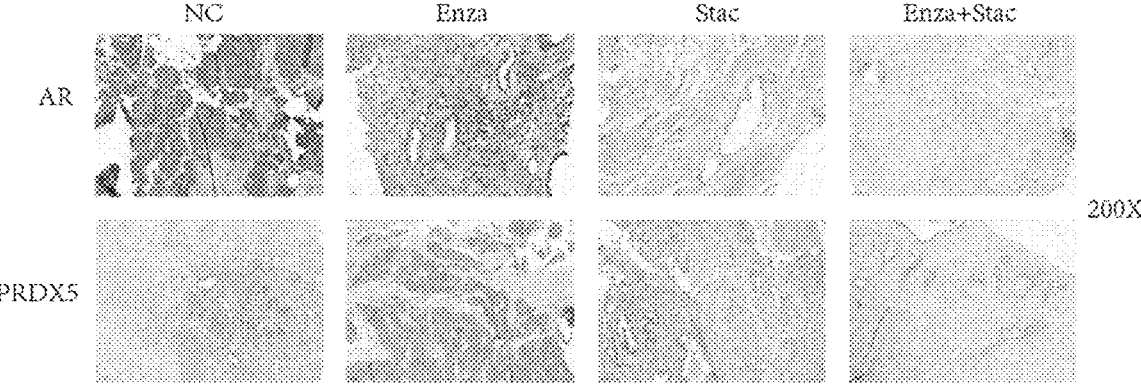
FIG. 6B shows PRDX5 and AR immunohistochemical graphs of the prostate tissue slices of mice in the Enza single-drug group 1 (10 mg/Kg), the Stac single-drug group 1 (80 mg/Kg) and the Enza and Stac combination group (10 mg/Kg+80 mg/Kg) in Example 3.
Figure 6C:
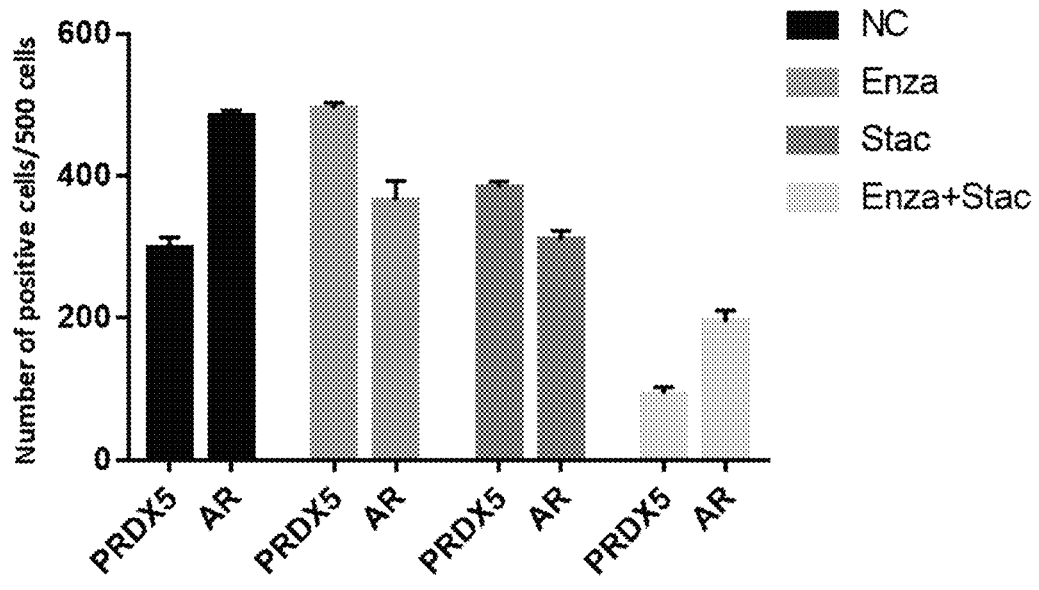
FIG. 6C shows a quantitative bar graph of immunohistochemical positive cells of mice in the Enza single-drug group 1 (10 mg/Kg), the Stac single-drug group 1 (80 mg/Kg) and the Enza and Stac combination group (10 mg/Kg+80 mg/Kg) in Example 3.

2. The results were shown in FIG. 5A to FIG. 5C and FIG. 6A to FIG. 6C. FIG. 5A to FIG. 5C are graphs showing drug combination effects of Enza, Stac and drug combination on changes in prostate weight of the C-MYC-over-expressed prostate cancer mouse model after generation of tolerance by continuous administration of Enza, and FIG. 5A shows a graph of changes in prostate weight of each group of mice with administration; FIG. 5B shows comparison photographs of stripped prostates of each group of mice; and FIG. 5C shows a graph of changes in weight of each group of mice with administration. FIG. 6A to FIG. 6C are graphs showing drug combination effects of Enza, Stac and drug combination scheme on the C-MYC-over-expressed prostate cancer mouse model after generation of tolerance by continuous administration of Enza, and FIG. 6A shows HE staining graphs of prostate tissue slices of each group of mice; and FIG. 6B and FIG. 6C respectively show AR and PRDX5 immunohistochemical graphs of the prostate tissue slices and a quantitative bar graph of positive cells of each group of mice.

An average of the prostate weights of the mice after continuous administration of Enza for 30 days was 43.9 mg, and at the moment, an average in the NC control group was 88.7 mg. The administration was continued, after 90 days, it was found that an average of the prostate weights of the mice in the Enza group was changed to 77.1 mg, and at the moment, an average in the NC control group was 98.2 mg, indicating that drug tolerance relapse was caused, resulting in CRPC. At the moment, the grouped administration was performed immediately to illustrate the drug combination effects.

The results of grouped combination and single use were shown in Table 1:

TABLE 1

Administration effects of different administrations
(30 d of administration) after drug tolerance relapse

| Administration | Average of prostate weights of mice |
|---|---|
| NC control group | 102.01 mg |
| Continued Enza single-drug group 1 (10 mg/Kg) after drug tolerance relapse | 54.42 mg |
| Continued Enza single-drug group 2 (90 mg/Kg) after drug tolerance relapse | 53.83 mg |
| Stac single-drug group 1 (80 mg/Kg Stac) after drug tolerance relapse | 50.86 mg |
| Stac single-drug group 2 (90 mg/Kg Stac) after drug tolerance relapse | 47.50 mg |
| Enza and Stac combination group (10 mg/Kg Enza + 80 mg/Kg Stac) after drug tolerance relapse | 37.07 mg |

It can be seen from FIG. 5A to FIG. 5C and Table 1 that the combination of Enza and Stac has a very significant effect compared with the single use of Enza and the single use of Stac, and the prostate weight can be reduced to about 37.068 mg. At the same time, it can be seen that the treatment effect of the single use of Stac was better than that of the single use of Enza after drug tolerance, indicating that the single use of Stac has an inhibiting effect on drug-tolerant CRPC.

It can be seen from the HE staining results of the tissue slices (FIG. 6A to FIG. 6C) that the prostate tumor of CRPC has obvious regression and fibrosis after drug combination, and it can be seen from immunohistochemistry that the combination of Enza and Stac significantly reduces the expressions of AR and PRDX5 compared with the single use of Enza and the single use of Stac, thereby proving that the combination effects were significant.

The results of grouped combination and single use were shown in Table 2:

TABLE 2

Administration effects of different administrations
(30 d of administration) after drug tolerance relapse

| Administration | AR expression/% | PRDX5 expression/% |
|---|---|---|
| NC control group | 93.7 | 47.0 |
| Continued Enza single-drug group 1 (10 mg/Kg) after drug tolerance relapse | 89.4 | 78.4 |
| Continued Enza single-drug group 2 (90 mg/Kg) after drug tolerance relapse | 82.6 | 80.0 |
| Stac single-drug group 1 (80 mg/Kg Stac) after drug tolerance relapse | 61.5 | 68.2 |
| Stac single-drug group 2 (90 mg/Kg Stac) after drug tolerance relapse | 57.4 | 60.9 |

TABLE 2-continued

Administration effects of different administrations
(30 d of administration) after drug tolerance relapse

| Administration | AR expression/% | PRDX5 expression/% |
|---|---|---|
| Enza and Stac combination group (10 mg/Kg Enza + 80 mg/Kg Stac) after drug tolerance relapse | 46.3 | 39.2 |

What is claimed is:

1. A method of preparing a composition for treating EPI-001 (EPI)-tolerant or enzalutamide (Enza)-tolerant castration-resistant prostate cancer (CRPC), comprising:
    providing Stachyose,
    providing an androgen receptor antagonist drug, and
    preparing the composition which consists of an effective amount of only the Stachyose and the androgen receptor antagonist drug as active agents, combined with a pharmaceutical excipient,
    wherein the androgen receptor antagonist drug is selected from the group consisting of: Enza, EPI, and a combination thereof,
    thereby preparing the composition for treating castration-resistant prostate cancer.

2. A method for treating EPI-001 (EPI)-tolerant or enzalutamide (Enza)tolerant castration-resistant prostate cancer (CRPC), comprising:
    administering an effective amount of a composition consisting of only Stachyose and an androgen receptor antagonist drug as active agents, combined with a pharmaceutical excipient, to an EPI/Enza-tolerant CRPC patient in need thereof,
    wherein the androgen receptor antagonist drug is selected from the group consisting of: Enza, EPI, and a combination thereof.

3. The method according to claim 1, wherein a mass ratio of the androgen receptor antagonist drug to the Stachyose in the composition is (1-8):1.

4. The method according to claim 1, wherein the pharmaceutical excipient is one or more of: a solvent, a propellant, a solubilizer, a cosolvent, an emulsifier, a colorant, an adhesive, a disintegrant, a filler, a lubricant, a wetter, an osmotic pressure regulator, a stabilizer, a glidant, a flavoring agent, a preservative, a suspending aid, a coating material, an aromatic agent, an anti-binding agent, an integration agent, a penetration enhancer, a pH regulator, a buffer, a plasticizer, a surfactant, a foamer, a defoamer, a thickener, an inclusion agent, a humectant, an absorbent, a diluent, a flocculant, a deflocculant, a filter aid, and a release retardant.

5. The method of preparation according to claim 1, wherein the method further comprises adding one or more carriers to the composition.

6. The method according to claim 5, wherein the one or more carriers are selected from: microcapsules, microspheres, nanoparticles, and liposomes.

7. The method according to claim 1, wherein the composition is in a dosage form of injections, lyophilized powder for injection, controlled-release injections, liposome injections, suspensions, implants, emboli, capsules, tablets, pills, or oral liquids.

* * * * *